United States Patent [19]

Tanaka

[11] Patent Number: 5,614,660
[45] Date of Patent: Mar. 25, 1997

[54] NOSE BAG APPLICATOR WITH PINHOLE CHECKER

[75] Inventor: Toshizumi Tanaka, Omiya, Japan

[73] Assignee: Fuji Photo Optical Co., Ltd., Omiya, Japan

[21] Appl. No.: 601,507

[22] Filed: Feb. 14, 1996

[30]  Foreign Application Priority Data

Feb. 24, 1995  [JP]  Japan ................................ 7-060026

[51] Int. Cl.⁶ .............................. A61B 1/00; A61B 10/00; A61M 5/00
[52] U.S. Cl. ........................ 73/37; 73/40; 600/115; 128/662.06; 604/165; 604/272
[58] Field of Search ................. 73/37, 40; 604/264, 604/280, 171, 165, 163, 272; 128/4, 772, 662.06; 600/115, 116

[56]  References Cited

U.S. PATENT DOCUMENTS

| | | | |
|---|---|---|---|
| 4,285,230 | 8/1981 | Hartness | 73/49.4 |
| 4,466,443 | 8/1984 | Utsugi | 128/660 |
| 4,708,014 | 11/1987 | Janitz | 73/37 |
| 4,815,470 | 3/1989 | Curtis et al. | 128/662.03 |
| 4,885,930 | 12/1989 | Werner et al. | 73/37 |
| 5,097,838 | 3/1992 | Hirooka et al. | 128/662.06 |
| 5,325,846 | 7/1994 | Szabo | 128/4 |
| 5,437,644 | 8/1995 | Nobles | 604/165 |
| 5,495,748 | 3/1996 | Brede et al. | 73/40 |

FOREIGN PATENT DOCUMENTS 6-32081  8/1994  Japan .

*Primary Examiner*—Hezron E. Williams
*Assistant Examiner*—J. David Wiggins
*Attorney, Agent, or Firm*—Oblon, Spivak, McClelland, Maier & Neustadt, P.C.

[57] ABSTRACT

A nose bag applicator for wrapping a balloon or a bag-like fluid-tight cover casing of elastic membranous material on a nose end of a rod-like insertion type internal examination instrument such as an ultrasound probe or ultrasound endoscope, the nose bag applicator including a pinhole checker for testing fluid tightness of the balloon or cover casing by the use of a pressure detector. The pressure detector is constituted by a pressure gauge adapted to monitor pressure variations in a hermetically closed space which is formed within a hollow cylindrical body of the nose bag applicator between a piston member and the balloon or cover casing hermetically fitted on a fore distal end portion of the cylindrical body. A pointer needle on the pressure gauge is deflected according to a pressure differential between the hermetically closed space and the atmospheric pressure.

6 Claims, 3 Drawing Sheets

NOSE BAG APPLICATOR WITH PINHOLE CHECKER

BACKGROUND OF THE INVENTION

1. Field of the Art

This invention relates generally to nose bag applicators for wrapping a balloon or a bag-shaped fluid-tight covering case of elastic membranous material on a nose end of rod-like insertion type internal examination instrument such as ultrasound probes, ultrasound scanners and ultrasound endoscopes, and more particularly to a nose bag applicator with a pinhole checker for testing fluid tightness of a balloon or bag-shaped elastic covering case to be put on a nose end of an insertion type internal examination instrument immediately before use.

2. Description of the Prior Art

For instance, insertion type ultrasound examination instruments such as ultrasound probes, ultrasound scanners and ultrasound endoscopes generally have an ultrasound transducer member mounted at a nose end of a flexible insertion rod to be introduced into an intracavitary portion of particular interest. Normally, a bag-shaped balloon is fitted on a nose end of the insertion rod in such a manner as to hermetically enclose a tip end section which supports an ultrasound transducer or transducers. Prior to an ultrasound examination, the balloon is filled and inflated with deaerated water or a suitable ultrasound transmission medium thereby to suppress attenuation of ultrasound signals and at the same time to secure a suitable standoff margin for the ultrasound transducer. Moreover, for the purpose of wrapping a balloon tightly on the insertion rod free of positional deviations in the course of insertion into an intracavitary region of examination, balloons of this sort are normally designed to have a diameter and a length which are, in a free deflated state, appreciably smaller than an outside diameter and an axial length of a nose end portion of an insertion rod, so that they more or less need to be stretched into a tensioned state when fitting on a nose end of an insertion rod. Accordingly, while in a deflated state before charging deaerated water or the other ultrasound transmissive medium, the balloon necessarily fits tightly on the surfaces around the circumference of the ultrasound insertion rod. Because of the tightness of a balloon in a fitted state and because of the necessity for fitting a fresh balloon on an insertion rod prior to each ultrasound examination, it is usually the case that the operator is required to undergo great efforts in a preparatory stage of an ultrasound examination for manually putting on a balloon on a nose end of an insertion rod to be used.

In an attempt to overcome the difficulties as mentioned above, there have been developed and introduced into use the so-called nose bag applicators which permit to put on balloons in a facilitated manner, for example, a piston and cylinder type nose bag applicator as proposed in Japanese Utility Model Publication H6-32081. In the case of the nose bag applicator of the publication just mentioned, a piston member is slidably fitted in a hollow cylindrical body which has an inside diameter larger than an outside diameter of a nose end of an ultrasound insertion rod to be used. A manual operating means is connected to the piston member to operate the same in directions inward and outward of the cylindrical body. An open end of a balloon, which is generally in the shape of a bag or sack, is hermetically fitted on a distal fore end portion of the cylindrical body in such a way as to form a closed space between the piston member and the balloon, so that, if the piston is pulled outward or toward the proximal end of the cylindrical body to expand the volume of the closed space, the balloon is sucked in and spread in a reversed state against the inner periphery of the cylindrical body under the influence of a negative pressure which is developed by the rearward expanding movement of the piston. In this state, a nose end portion of an ultrasound insertion rod is put into the cylindrical body which holds the balloon against its inner periphery, and then the open end portion of the balloon is detached from the fore distal end of the cylindrical body, letting the balloon fit tightly on the nose end portion of the insertion rod in an extremely facilitated manner.

At the time of wrapping a balloon on a nose end of an insertion rod in a preparatory stage of an ultrasound examination in the above-described manner, the balloon which is formed of a thin film-like membranous material might contain a pinhole or a similar defect which is detrimental to hermetical tightness of the balloon. Of course, all of balloons of this sort are usually tested for hermetic tightness before shipping, but there are still the possibilities of the balloons picking up pinholes or other defects while being handled after shipping, let alone the minute pinholes which have been overlooked in a quality check. Should a balloon wrapped on an ultrasound insertion rod contain a pinhole, it is very likely that liquid leaks through the pinhole occur upon pumping deaerated water or another ultrasound transmissive medium into the balloon after insertion into an intracavitary region to be examined. Taking into account the fact that an ultrasound transmissive medium is normally fed under a relatively high pressure, it could enlarge the pinhole to magnify the extent of liquid leaks, resulting in total deflation of the balloon especially in case of an examination which extends over a relatively long time.

Moreover, in some cases a covering case of rubber or other elastic membranous material is fitted on an ultrasound insertion rod for the purpose of preventing contamination of the rod. In such a case, the covering case should also be able to maintain hermetic tightness since otherwise the surfaces of the insertion rod would be contaminated with intruding body fluids. However, as a matter of fact it has been difficult to spot minute defects like pinholes in a covering case simply by visual observation at the time of wrapping it on an insertion rod, despite dangerous situations which can result, such as proliferation of germs in unknowingly contaminated areas of an insertion rod. Therefore, from a hygienic point of view, It is desirable also for such covering cases to be tested for fluid tightness by a pinhole check immediately before use.

SUMMARY OF THE INVENTION

In view of the foregoing situations, it is an object of the present invention to provide a nose bag applicator for wrapping a bag-shaped fluid-tight casing of elastic membranous material on a nose end of a rod-like insertion type medical examination instrument or of a rod-like instrument of a similar nature, the bag applicator incorporating a pinhole checker enabling an operator to test the covering case immediately before use for a pinhole or a similar defect which would ruin fluid tightness of the casing.

In accordance with the present invention, the foregoing objective is achieved by the provision of a nose bag applicator for wrapping a bag-shaped fluid-tight covering case of elastic membranous material on a nose end of a rod-like insertion type internal examination instrument or the like, the nose bag applicator including: a hollow cylindrical body having an inside diameter larger than an outside diameter of a nose end portion of the examination instrument to be wrapped in the covering case and capable of holding on a fore end portion thereof an opening at one end of the covering case in a hermetically sealed state; a piston member slidably received in the cylindrical body for forward and rearward movements in hermetic sliding contact with inner peripheral surfaces of the cylindrical body, the piston member being moved in a rearward direction to draw in and spread the covering case against inner peripheral surfaces of the cylindrical body by a suction force from a negative pressure developed by the rearward movement of the piston member in a hermetically closed space formed within the cylindrical body between the piston member and the covering case fitted on the fore end portion of the cylindrical body, holding the covering case in a spread state to receive a nose end portion of said examination instrument therein; and a pressure detector means mounted on the cylindrical body in communication with the hermetically closed space to check for pressure variations in the hermetically closed space.

Upon fitting an open end of a bag-like case of elastic membranous material hermetically on a fore tip end portion of the cylindrical body, a closed space is formed in the cylindrical body between the fore end face of the piston member and the bag-like case which is still in a deflated or shrunk state. As the piston is pulled backward toward the rear end of the cylindrical body, the closed space is expanded to undergo pressure reductions below the atmospheric pressure level outside the cylindrical body. As a consequence, the elastic case is sucked into the cylindrical body and spread against the inner periphery of the latter under the influence of the negative pressure developed in the closed space. After a rearward retracting movement over a predetermined distance, the piston is temporarily retained in a retracted position, leaving the elastic case within the cylindrical body, and a nose end of the rod-like examination instrument is inserted into the bag-like case which is spread against the inner periphery of the cylindrical body. In this state, the pressure detector means, which is in communication with the closed space, normally stays at a constant level in terms of a pressure reading. However, in case the flexible membranous material of the case contains a pinhole or a similar defect, air flows into the closed space within the cylindrical body, causing variations to the pressure level which is detected by the pressure detector means. Therefore, defective air tightness due to a pinhole or a similar flaw can be easily detected from the readings of the pressure detector means. Since each bag-like case is checked for fluid tightness by the above-described pinhole checker immediately before it is turned over to and wrapped on a nose end portion of a rod-like examination instrument, there is little possibility of the elastic case being damaged and losing fluid tightness during an internal examination which follows.

The above and other objects, features and advantages of the invention will become apparent from the following particular description, taken in conjunction with the accompanying drawings which show by way of example preferred embodiments of the invention.

DESCRIPTION OF PREFERRED EMBODIMENTS

Figure 1:
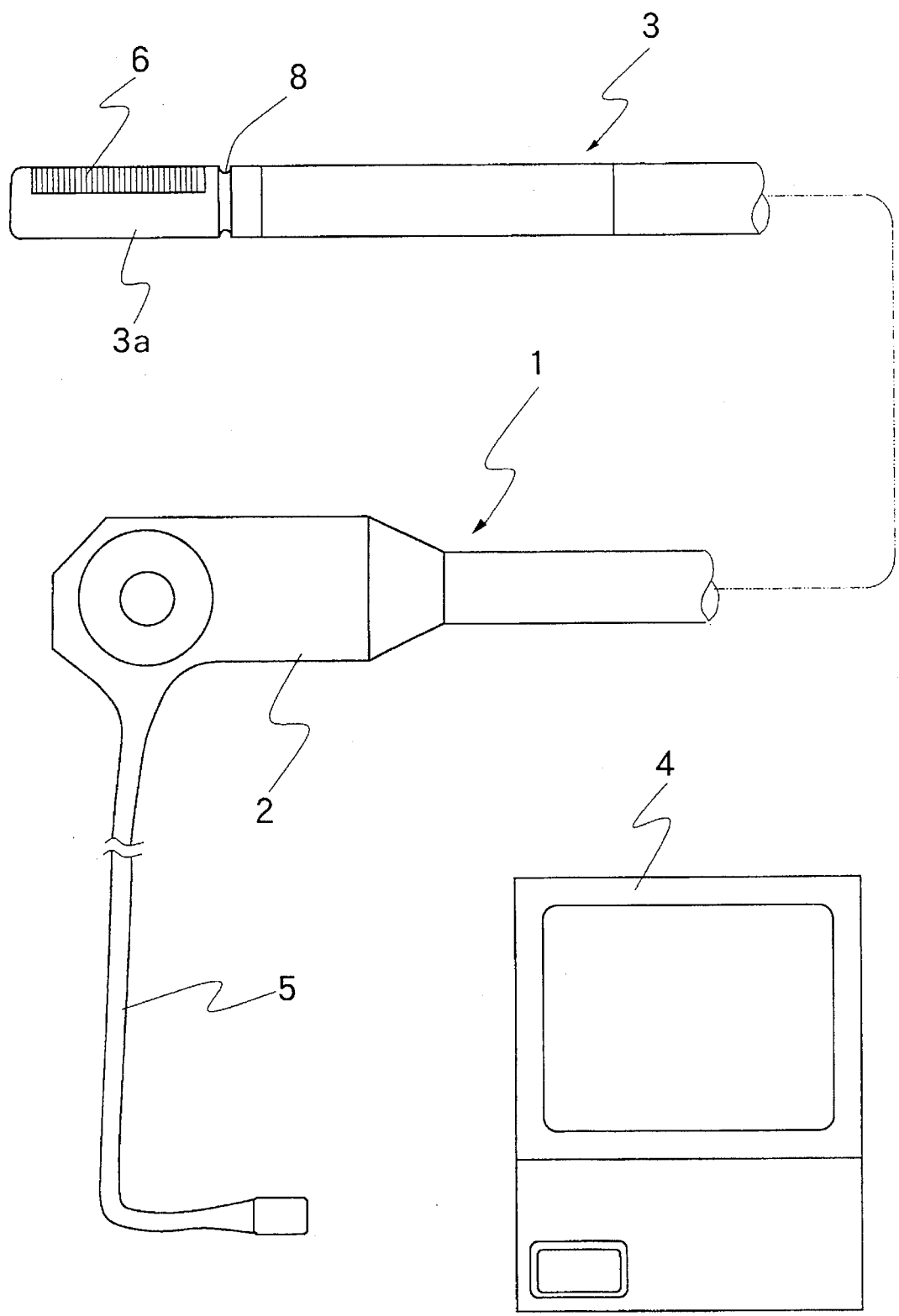
FIG. 1 is a schematic illustration of general layout of an ultrasound examination system, which is shown as a typical example of a rod-like insertion type instrument to be wrapped in a balloon or a bag-like covering case of elastic membranous material at its nose end by the use of a nose bag applicator according to the present invention.

Hereafter, the invention is described more particularly by way of its preferred embodiments shown in the drawings.

Referring to FIG. 1, there is shown an ultrasound probe 1 as an example of the insertion type internal examination instruments. The ultrasound probe 1 is largely constituted by a manipulating head assembly 2 to be gripped and manipulated by an operator, an elongated flexible insertion rod 3 extended out on the front side of the manipulating head assembly 2, and a cable 5 led out on the rear side of the manipulating head assembly 2 to connect the same to an ultrasound image observation terminal 4. Except for a short tip end section 3a which supports thereon an ultrasound transducer 6, the ultrasound insertion rod 3 is constructed of flexible or pliable component parts in a manner well known in the art. In the particular example shown, the ultrasound transducer 6 consists of a large number of ultrasound transducer elements which are arranged in a row in the axial direction of the insertion rod, and are sequentially actuated for an electronic linear or convex scanning operation.

Figure 2:
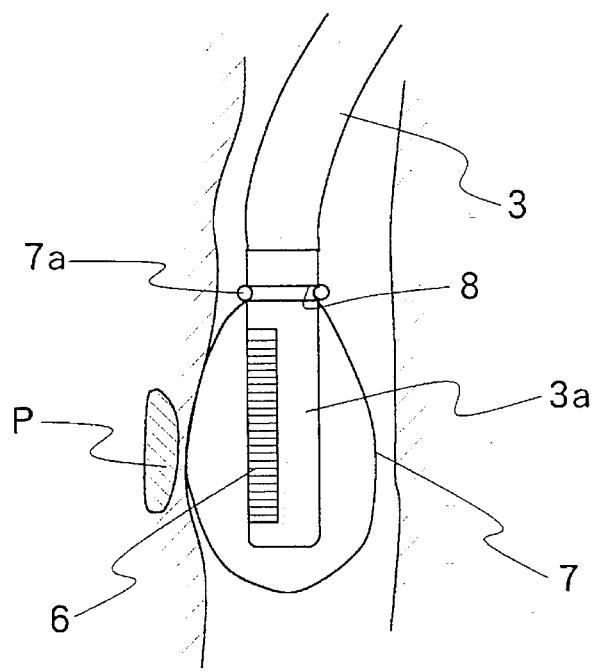
FIG. 2 is a schematic view of a balloon fitted on a nose end portion of a rod-like ultrasound probe inserted into an intracavitary portion for a scanning operation.

For instance, in a case where the ultrasound probe 1 is used for scanning a region P immediately under the mucous membrane of a digestive tract as shown particularly in FIG. 2, the tip end section 3a at the nose end of the insertion rod 3 is inserted through the digestive tract and located in a scanning position where the ultrasound transducer 6 faces the subject region P of ultrasound examination. Prior to insertion into an intracavitary region of interest, a balloon 7 is usually fitted on the tip end section 3a of the insertion rod 3 for the purpose of locating and keeping the ultrasound transducer 6 in a standoff position relative to the subject region P. For the purpose just mentioned and for suppressing attenuation of ultrasound signals to a minimum during a scanning operation at the standoff position, the balloon 7 is maintained in an inflated state by charging deaerated water or other suitable ultrasound transmissive fluid medium which is supplied through a fluid supply duct (not shown).

In this instance, the balloon 7 is made of a thin membranous material which has satisfactory acoustic properties in terms of transmission of ultrasound signals, along with suitable properties in elasticity, for example, like a latex membrane. The balloon 7 is closed at one end and open at the other end in the fashion of a bag or the like. The open end of the balloon 7 is hemmed with an anchor ring 7a which is substantially of a circular shape in section. This anchor ring 7a is designed to be fixedly and hermetically anchored in an annular groove 8 which is provided on the circumference of the tip end section 3a of the ultrasound insertion rod 3 at a position on the proximal side of the ultrasound transducer 6.

When charged with deaerated water, the balloon 7 is inflated to a predetermined degree as shown in FIG. 2. However, before charging deaerated water, it is in a shrunk or deflated state tightly fitting on the circumference of the tip end section 3a of the ultrasound insertion rod 3, tight enough for resisting against positional deviations which would otherwise occur by contact with intracavitary walls in the course of insertion of the ultrasound probe rod. Therefore, in a free shrunk state, the balloon 7 is conspicuously smaller in diameter and length as compared with the tip end section 3a at the nose end of the insertion rod 3, namely, conspicuously smaller as compared with the outside diameter of and the length from the annular groove 8 to the fore distal end of the tip end section 3a. Therefore, at the time of fitting the balloon 7 on the tip end section 3a of the insertion rod 3, it needs to be stretched in both radial and longitudinal directions. Besides, the operator has to replace the balloon 7 each time prior to an examination, fitting a fresh one on the rigid tip end section 3a of the ultrasound insertion rod 3 before diagnosing each patient by the use of the ultrasound probe.

Figure 3:
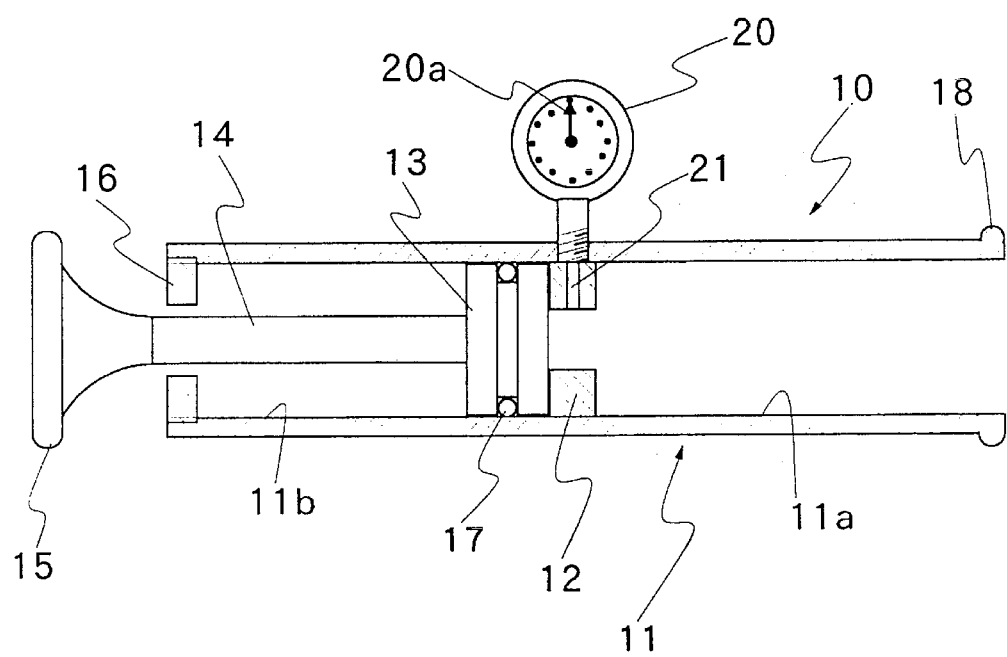
FIG. 3 is a schematic longitudinal section of the nose bag applicator.
Figure 4:
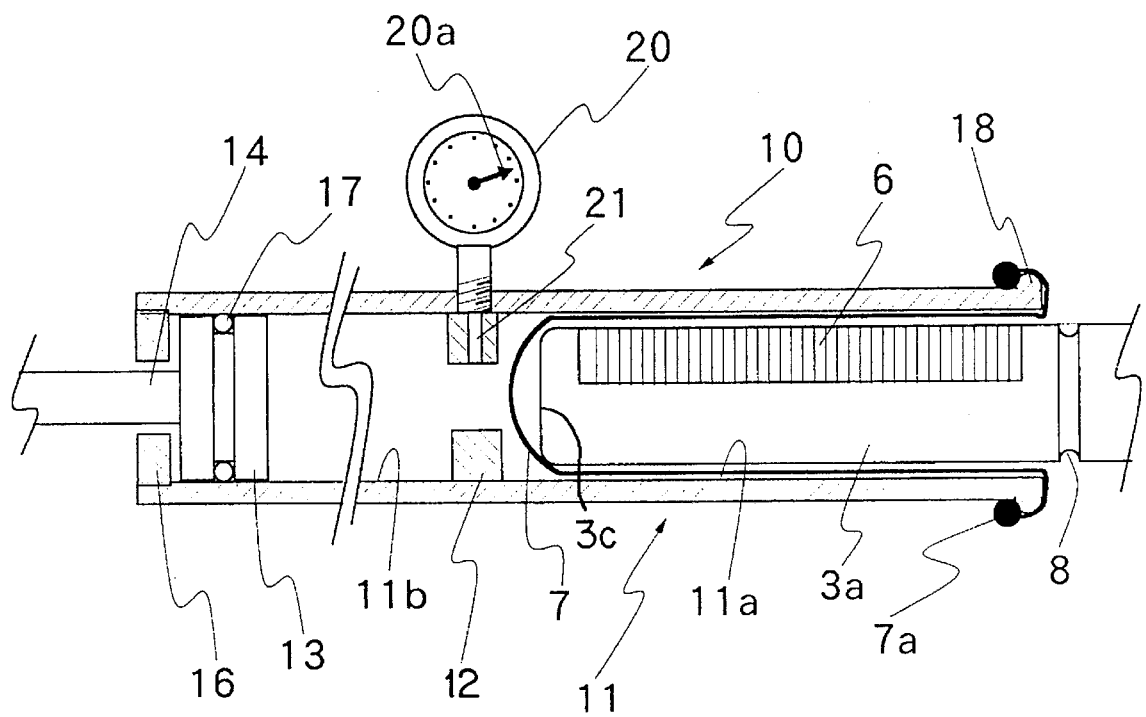
FIG. 4 is a view similar to FIG. 3, but showing an automatic and tool-aided operation of wrapping a balloon on a nose end portion of the rod-like ultrasound probe.
Figure 5:
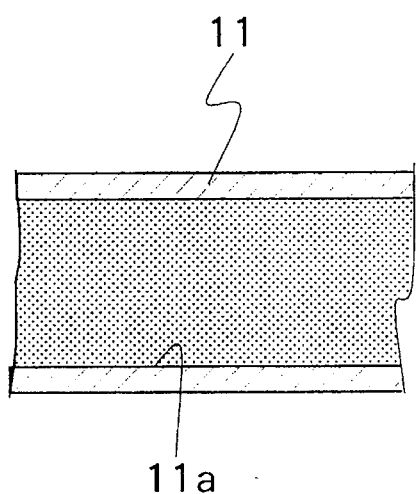
FIG. 5 is a fragmentary sectional view of a balloon receptacle chamber within a cylindrical body of the nose bag applicator.

Shown in FIGS. 3 to 5 is a nose bag applicator 10 which has been resorted to for facilitating the job of wrapping a nose end of a rod-like examination instrument with a shrunken balloon 7, which is normally extremely troublesome to handle. This nose bag applicator 10 basically includes a rigid hollow cylindrical body 11 which is formed of a metal or synthetic resin material and has an inside diameter larger than the outside diameter of, for example, the tip end section 3a at the nose end of the ultrasound insertion rod 3. Besides, the cylindrical body 11 has a length at least double the axial length of the tip end section 3a from the annular groove 8 to its fore distal end. The hollow cylindrical body 11 is internally provided with an annular radial partition wall 12 substantially at an median point of its length, the partition wall 12 dividing the interior of the cylindrical body 11 into a fore balloon receptacle chamber 11a and a rear operating chamber 11b. Slidably and hermetically fitted in the rear operating chamber 11b is a piston member 13 with an operating rod 14 which can be manually operated to move the piston 13 within the rear operating chamber 11b toward and away from the radial partition wall 12. For this purpose, a grip handle 15 is provided at the outer end of the operating rod 14, which is led out through the rear end of the cylindrical body 11, so that the operator can move the piston 13 toward and away from the partition wall 12 by moving the grip handle 15 back and forth. Indicated at 16 is a stopper ring which is fitted in the rear end of the cylindrical body 11 to delimit the stroke length of the piston 13. Accordingly, the piston 13 is movable back and forth between the radial partition wall 12 and the rear stopper ring 16 in hermetical sliding contact with the inner peripheral surfaces of the operating chamber 11b. Reference numeral 17 indicates a seal member which is fitted on the circumferential surface of the piston 13.

The anchor ring 7a around the open end of the balloon 7 is hermetically fitted on a distal end portion of the cylindrical body 11 through tight engagement with the circumferential surface of the latter. In doing so, the anchor ring 7a needs to be stretched wide enough to pass over an annular stopper rim 18 which is provided at the distal end of the cylindrical body 11 to retain the anchor ring 7a in position on the cylindrical body 11. The anchor ring 7a needs to be relocated afterwards in the annular groove 8 on the part of the tip end section 3a of the ultrasound insertion rod 3, riding over the stopper rim 18, for wrapping the balloon 7 on the nose end of the latter, the stopper rim 18 is limited in height to such a range where it can hold the anchor ring 7a securely in position on the cylindrical body 11 but permits to move the anchor ring 7a thereover quite smoothly upon application of a suitable external force at the time of relocation onto the tip end section 3a of the insertion rod 3.

By the use of the nose bag applicator 10 as described above, a balloon 7 can be fitted on the rigid tip end section 3a at the nose end of the ultrasound insertion rod 3 quite easily. More specifically, after locating the piston 13 in a position in the proximity of or in abutting engagement with the radial partition wall 12, the anchor ring 7a at the open end of the balloon 7 is fitted on the cylindrical body 11 on the rear side of the stopper rim 18, hermetically closing the balloon receptacle chamber 11a, more precisely, hermetically closing a space which is defined between the fore end face of the piston 13 and the balloon 7. Since the piston 13 is slidable back and forth within the cylindrical body 11, the just-mentioned closed space is expanded or contracted depending upon the direction of sliding movement of the piston 13. As the grip handle 15 is pulled to move the piston 13 rearward within and along the inner periphery of the cylindrical body 11 away from the radial partition wall 12, the closed space is expanded according to the volume of displacement experienced by the piston 13, developing a negative pressure therein. Therefore, upon a rearward sliding movement of the piston 13, the balloon 7 which is made of an elastic membranous material is sucked into the cylindrical body 11 and spread outward against the inner periphery of the balloon receptacle chamber 11a before the piston 13 comes into abutment against the stopper ring 17 at the rear end of the cylindrical body 11.

While the balloon 7 is spread within the balloon receptacle chamber 11a of the cylindrical body 11 in this manner, the tip end section 3c at the nose end of the ultrasound insertion rod 3 is put into the balloon receptacle chamber 11a as shown in FIG. 4. At this time, the tip end section 3c which has an outside diameter smaller than the inside diameter of the balloon receptacle chamber 11a of the 18 cylindrical body 11 can be inserted into the latter substantially out of contact with the balloon 7 which is spread against the inner periphery of the balloon receptacle chamber 11a of the cylindrical body 11. Accordingly, there is almost no possibility of the balloon 7 getting bruised or damaged to any serious degree by sliding contact with the tip end section 3c of the ultrasound insertion rod 3. As soon as the tip end section 3c is put in the cylindrical body 11 up to a position near the annular groove 8, the piston 13 is once moved in an inward direction toward the radial partition wall 12. By so doing, the pressure in the closed space is elevated beyond the atmospheric pressure level, pushing the balloon 7 off the inner periphery of the balloon receptacle chamber 11a and at the same time urging same into intimate engagement with the circumference of the tip end section 3c of the ultrasound insertion rod 3. In this regard, in case the difference between the outside diameter of the ultrasound observation section 3c and the inside diameter of the cylindrical body 11 is minimized to a least possible value, the balloon 7 is urged to engage with the tip end section 3c gradually from the fore end of the latter which is in the deepest part of the balloon receptacle chamber 11a, in such a manner as to preclude air trapping between the balloon 7 and the tip end section 3c of the ultrasound insertion rod 3. Thereafter, the anchor ring a is removed from the stopper rim 18 and fitted in the annular groove 8 on the tip end section 3c of the insertion rod 3. Accordingly, the balloon 7 which is now wrapped on the tip end section 3c comes out upon extracting the ultrasound insertion rod 3 from the cylindrical body 11.

As mentioned hereinbefore, in case of balloons 7 consisting of thin fluid-tight membranous material, it is desirable to test each balloon 7 for fluid tightness by a pinhole check in a suitable stage of fabrication process and also immediately before wrapping same on an ultrasound insertion rod 3. As the defects of this sort are too small to spot visually, it is probable that a balloon with a pinhole or pinholes is unknowingly wrapped on an ultrasound insertion rod 3.

In order to solve this problem, the nose bag applicator 10 according to the present invention is provided with a pinhole checker mechanism which makes it possible to test each balloon 7 for fluid tightness immediately before use, checking for a pinhole or a similar flaw which would ruin the fluid tightness of the balloon 7. The pinhole checker mechanism includes a pressure detector means in the form of a pressure gauge 20 which is mounted on the cylindrical body 11, and arranged to detect the pressure in the closed space which is formed in the cylindrical body 11 of the nose bag applicator between the piston 13 and a balloon 7 hermetically fitted on the fore end of the cylindrical body 11, through a pressure sampling conduit which is formed, for example, in the radial partition wall 12. In this instance, the pressure gauge 20 is provided with a pointer needle 20a which is turned on a dial face to indicate a pressure difference across the membrane of the balloon 7, namely, a difference between the atmospheric pressure outside the balloon 7 and a pressure prevailing in the above-mentioned closed space within the cylindrical body 11. Normally, as the piston 13 is pulled outward and stopped at a predetermined position, the pressure in the closed space is maintained substantially at a constant level unless an air flow takes place through a pinhole or a similar defect. If there is a pinhole in the balloon 7, air flows into the closed space in the cylindrical body 11 therethrough, putting the pointer needle 20a of the pressure gauge 20 in deflecting movements. Accordingly, simply by viewing the movements of the pointer needle 20a, one can check the fluid tightness of each balloon 7 immediately before use or installation of a balloon onto the insertion rod.

In this regard, it is necessary to take into account the possibilities that a pinhole in a balloon 7 could be hermetically closed by intimate contact with the inner surface of the balloon receptacle chamber 11a, blocking air flows and as a result deceiving the operator by not deflecting the pointer needle 20a as if there were no pinholes. In order to prevent the occurrences of such situations, it is desirable to lessen the intimacy of the contacting engagement by roughening the inner surface of the balloon receptacle chamber 11a to a certain degree. For instance, for this purpose, the balloon receptacle chamber 11a may be interiorly provided with a non-smooth satin finish surface which contains minute peaks and valleys over its entire area as shown in FIG. 5. These minute peaks and valleys function to prevent a balloon 7 from hermetically or tightly engaging with the inner surface of the balloon receptacle chamber 11a, thereby ensuring the detection pinholes, if any, at a high accuracy rate. After the pinhole check, the anchor ring 7a which is in engagement with the stopper rim 18 is simply relocated into the annular groove 8 on the ultrasound observation end 3c of the insertion rod 3. Therefore, there is substantially no possibilities of the balloon 7 being punctured before or during an examination which follows. Namely, the checkup of fluid tightness at this point has great significance in accuracy and reliability.

In the foregoing embodiment, the nose bag applicator with the pinhole checker according to the present invention has been described and shown by way of operations of wrapping a balloon on a nose end of an ultrasound insertion rod and inflating the balloon by a charge of an ultrasound transmissive medium in such a manner as to surround an ultrasound transducer element on a tip end section of the insertion rod. Similarly, the nose bag applicator of the invention can be used for checking and wrapping a fluid-tight protective covering case of membranous material on an insertion rod of an endoscope for the purpose of preventing contamination of rod portions to be introduced into an intracavitary region. Further, according to the invention, it is not necessarily required to provide the radial partition wall which divides the cylindrical body of the nose bag applicator into a fore balloon receptacle chamber and a rear operating chamber. In case the partition wall is absent, the pressure in the closed space can be detected at any other position on the cylindrical body or the piston as long as it does not impede the pinhole check. Furthermore, although a single anchor ring is provided on each balloon in the foregoing embodiment, another anchor ring may be added at the other end of the balloon for fitting engagement in another annular groove which is provided on the insertion rod at a position close to the fore distal end of the tip end section. Moreover, in order to prevent a balloon from hermetically contacting the inner surface of the balloon receptacle chamber, a multitude of finely pitched grooves may be formed in perpendicularly or obliquely crossing directions on the inner periphery of the balloon receptacle chamber, instead of the above-described satin finish surface which contain minute ups and downs.

As described above, the nose bag applicator according to the present invention integrally incorporates a pinhole checker which is arranged to detect a pinhole or a similar defect in a balloon or a bag-like fluid-tight covering case of elastic membranous material by way of pressure variations in a closed space formed within a cylindrical body of the applicator upon fitting thereon the balloon or covering case, permitting testing of the balloon or covering case for fluid tightness immediately before wrapping same on a nose end portion of a rod-like insertion type examination instrument in an accurate and reliable manner.

What is claimed is:

1. A nose bag applicator for wrapping a bag-shaped fluid-tight covering case of elastic membranous material on a nose end of a rod-like insertion type internal examination instrument or the like, said nose bag applicator including:

a hollow cylindrical body having an inside diameter larger than an outside diameter of a nose end portion of said rod-like examination instrument to be wrapped in said covering case and holding said covering case at a fore end portion of said cylindrical body via an opening at one end of said covering case in a hermetically sealed state;

a piston member slidably received in said cylindrical body, said piston member being movable in forward and rearward directions in hermetic sliding contact with inner peripheral surfaces of said cylindrical body, said piston member being movable in said rearward direction to draw in and spread by expansion said covering case against inner peripheral surfaces of said cylindrical body by a negative pressure developed by the rearward movement of said piston member in a hermetically closed space formed within said cylindrical body between said covering case and said piston member, said cylinder body holding said covering case in a spread state to receive a nose end portion of said examination instrument therein; and detector means mounted on said cylindrical body in fluid communication with said hermetically closed space for checking for pressure variations in said hermetically closed space, said pressure detector means detecting leaks in said bag-shaped covering case while sealed in said nose bag applicator and before being installed onto the nose end portion of said rod-like examination instrument.

2. A nose bag applicator as defined in claim 1, wherein said cylindrical body of said nose bag applicator is internally divided by an annular partition wall into a front chamber and a rear chamber, said front chamber being provided with roughened surfaces with minute peaks and valleys on the inner periphery thereof for loose abutting contact with said covering case so as to facilitate leak detection of any possible airholes formed in said bag-shaped covering case while expanded into radial contact with the circumferential wall of said cylindrical body while said rear chamber is provided with smoothly finished surfaces on the inner periphery thereof for hermetic sliding contact with said piston member.

3. A nose bag applicator as defined in claim 2, wherein said pressure detector means comprises a pressure gauge mounted on said cylindrical body of said nose bag applicator and communicated with said hermetically closed space in said cylindrical body through a pressure tapping conduit formed radially through said partition wall, said pressure gauge having a pointer needle which is deflectable due to a pressure differential between said hermetically closed space and atmospheric pressure.

4. A nose bag applicator for wrapping a bag-shaped fluid-tight covering case of elastic membranous material on a nose end of a rod-like insertion type internal examination instrument or the like, said nose bag applicator including:

a hollow cylindrical body having an inside diameter larger than an outside diameter of a nose end portion of said rod-like examination instrument to be wrapped in said covering case and holding said covering case at a fore end portion of said cylindrical body via an opening at one end of said covering case in a hermetically sealed state;

a piston member slidably received in said cylindrical body, said piston member being movable in forward and rearward directions in hermetic sliding contact with inner peripheral surfaces of said cylindrical body, said piston member being movable in said rearward direction to draw in and spread by expansion said covering case against inner peripheral surfaces of said cylindrical body by a negative pressure developed by the rearward movement of said piston member in a hermetically closed space formed within said cylindrical body between said covering case and said piston member, said cylinder body holding said covering case in a spread state to receive a nose end portion of said examination instrument therein; and a pressure detector mounted on said cylindrical body in fluid communication with said hermetically closed space, said pressure detector checking for pressure variations in said hermetically closed space and detecting leaks in said bag-shaped covering case while sealed in said nose bag applicator and before being installed onto the nose end portion of said rod-like examination instrument.

5. A nose bag applicator as defined in claim 4, wherein said cylindrical body of said nose bag applicator is internally divided by an annular partition wall into a front chamber and a rear chamber, said front chamber being provided with roughened surfaces with minute peaks and valleys on the inner periphery thereof for loose abutting contact with said covering case so as to facilitate leak detection of any possible airholes formed in said bag-shaped covering case while expanded into radial contact with the circumferential wall of said cylindrical body while said rear chamber is provided with smoothly finished surfaces on the inner periphery thereof for hermetic sliding contact with said piston member.

6. A nose bag applicator as defined in claim 5, wherein said pressure detector comprises a pressure gauge mounted on said cylindrical body of said nose bag applicator and communicated with said hermetically closed space in said cylindrical body through a pressure tapping conduit formed radially through said partition wall, said pressure gauge having a pointer needle which is deflectable due to a pressure differential between said hermetically closed space and atmospheric pressure.

* * * * *